US008885163B2

(12) United States Patent
Morys et al.

(10) Patent No.: US 8,885,163 B2
(45) Date of Patent: Nov. 11, 2014

(54) INTERFEROMETRY-BASED DOWNHOLE ANALYSIS TOOL

(75) Inventors: Marian L. Morys, Downingtown, PA (US); Steve Zannoni, Houston, TX (US); Christopher M. Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/147,478

(22) PCT Filed: Dec. 23, 2009

(86) PCT No.: PCT/US2009/069492
§ 371 (c)(1),
(2), (4) Date: Aug. 2, 2011

(87) PCT Pub. No.: WO2011/078869
PCT Pub. Date: Jun. 30, 2011

(65) Prior Publication Data
US 2012/0250017 A1    Oct. 4, 2012

(51) Int. Cl.
*G01N 15/02*    (2006.01)
*G01B 9/02*    (2006.01)
(Continued)

(52) U.S. Cl.
CPC ............ *G01N 21/31* (2013.01); *G01N 21/3577* (2013.01); *G01N 21/35* (2013.01);
(Continued)

(58) Field of Classification Search
CPC .................. G01N 33/2823; G01N 2010/3595; G01N 21/3581; G01N 21/31; G01N 21/3577; G01N 21/33; G01N 21/35; G01B 9/02; G01J 3/12
USPC ............... 356/450–456, 241, 1, 241.3, 241.4, 356/241.5; 250/339.11
See application file for complete search history.

(56) References Cited

U.S. PATENT DOCUMENTS 2,757,300 A    7/1956    Laidig
(Continued)

FOREIGN PATENT DOCUMENTS

AU    2009356978    6/2011
GB    177816    3/1922
(Continued)

OTHER PUBLICATIONS

Adur, Rohan "Using Single Nitrogen-Vacancy Centers in Diamond Nanocrystals for Sensitive Sensing of Weak Magnetic Fields with Nanoscale Resolution", Ohio State Physics Term Paper, circa 2009, 4 pgs.
(Continued)

*Primary Examiner* — Tarifur Chowdhury
*Assistant Examiner* — Sunghee Y Gray
(74) *Attorney, Agent, or Firm* — Krueger Iselin LLP; Benjamin Fite

(57) ABSTRACT

Various systems and methods for performing optical analysis downhole with an interferogram (a light beam having frequency components with a time variation that identifies those frequency components. The interferogram is produced by introducing an interferometer into the light path, with the two arms of the interferometer having a propagation time difference that varies as a function of time. Before or after the interferometer, the light encounters a material to be analyzed, such as a fluid sample from the formation, a borehole fluid sample, a core sample, or a portion of the borehole wall. The spectral characteristics of the material are imprinted on the light beam and can be readily analyzed by processing electronics that perform a Fourier Transform to obtain the spectrum or that enable a comparison with one or more templates. An interferometer designed to perform well in the hostile environments downhole is expected to enable laboratory-quality measurements.

22 Claims, 5 Drawing Sheets

(51) Int. Cl.
*G01J 3/45* (2006.01)
*G01J 5/02* (2006.01)
*G01N 21/35* (2014.01)
*E21B 49/08* (2006.01)
*G01N 21/31* (2006.01)
*G01N 21/33* (2006.01)

(52) U.S. Cl.
CPC .............. *E21B 49/088* (2013.01); *G01N 21/33* (2013.01); *G01N 2021/3595* (2013.01)
USPC ........... 356/335; 356/450; 356/451; 356/452; 356/453; 356/454; 356/455; 356/456; 250/339.11

(56) References Cited

U.S. PATENT DOCUMENTS

| | | | |
|---|---|---|---|
| 2,972,251 A | 2/1961 | Harper | |
| 3,449,546 A | 6/1969 | Dhoble | |
| 4,103,174 A | 7/1978 | McClatchie et al. | |
| 4,160,929 A | 7/1979 | Thorington et al. | |
| 4,499,955 A | 2/1985 | Campbell et al. | |
| 4,774,396 A | 9/1988 | Salit et al. | |
| 4,802,761 A * | 2/1989 | Bowen et al. | 356/301 |
| 4,839,516 A * | 6/1989 | Freeman et al. | 250/255 |
| 4,994,671 A | 2/1991 | Safinya et al. | |
| 4,996,421 A * | 2/1991 | Rai et al. | 250/255 |
| 5,161,409 A * | 11/1992 | Hughes et al. | 73/152.19 |
| 5,166,747 A | 11/1992 | Schroeder et al. | |
| 5,258,620 A * | 11/1993 | Sueyasu et al. | 250/339.12 |
| 5,284,054 A * | 2/1994 | Loebach | 73/23.3 |
| 5,331,399 A * | 7/1994 | Tank et al. | 356/455 |
| 5,341,207 A * | 8/1994 | Tank et al. | 356/455 |
| 5,360,738 A * | 11/1994 | Jones et al. | 436/30 |
| 5,368,669 A | 11/1994 | Maine et al. | |
| 5,457,259 A * | 10/1995 | Elgarhy et al. | 442/93 |
| 5,621,523 A | 4/1997 | Oobayashi et al. | |
| 5,790,432 A | 8/1998 | Morys | |
| 5,939,717 A | 8/1999 | Mullins | |
| 5,946,641 A | 8/1999 | Morys | |
| 6,006,844 A | 12/1999 | Van Puymbroeck et al. | |
| 6,040,191 A * | 3/2000 | Grow | 506/12 |
| 6,162,766 A | 12/2000 | Muir et al. | |
| 6,178,815 B1 | 1/2001 | Felling et al. | |
| 6,181,427 B1 | 1/2001 | Yarussi et al. | |
| 6,220,371 B1 | 4/2001 | Sharma et al. | |
| 6,268,726 B1 | 7/2001 | Prammer et al. | |
| 6,325,146 B1 | 12/2001 | Ringgenberg et al. | |
| 6,350,986 B1 | 2/2002 | Mullins et al. | |
| 6,362,619 B2 | 3/2002 | Prammer et al. | |
| 6,378,364 B1 | 4/2002 | Pelletier et al. | |
| 6,403,949 B1 * | 6/2002 | Davis et al. | 250/227.27 |
| 6,437,326 B1 | 8/2002 | Yamate et al. | |
| 6,446,719 B2 | 9/2002 | Ringgenberg et al. | |
| 6,446,720 B1 | 9/2002 | Ringgenberg et al. | |
| 6,465,775 B2 | 10/2002 | Mullins et al. | |
| 6,518,756 B1 | 2/2003 | Morys et al. | |
| 6,527,052 B2 | 3/2003 | Ringgenberg et al. | |
| 6,543,281 B2 | 4/2003 | Pelletier et al. | |
| 6,583,621 B2 | 6/2003 | Prammer et al. | |
| 6,688,176 B2 | 2/2004 | Storm et al. | |
| 6,729,398 B2 | 5/2004 | Ringgenberg et al. | |
| 6,748,328 B2 | 6/2004 | Storm et al. | |
| 6,755,079 B1 | 6/2004 | Proett et al. | |
| 6,765,384 B2 | 7/2004 | Morys | |
| 6,768,105 B2 | 7/2004 | Mullins et al. | |
| 6,788,066 B2 | 9/2004 | Wisler et al. | |
| 6,825,659 B2 | 11/2004 | Prammer et al. | |
| 6,853,452 B1 | 2/2005 | Laufer | |
| 6,888,127 B2 | 5/2005 | Jones et al. | |
| 6,912,904 B2 | 7/2005 | Storm et al. | |
| 6,956,204 B2 | 10/2005 | Dong et al. | |
| 6,967,322 B2 | 11/2005 | Jones et al. | |
| 6,967,722 B2 | 11/2005 | Manning | |
| 6,975,112 B2 | 12/2005 | Morys et al. | |
| 7,021,375 B2 | 4/2006 | Ringgenberg et al. | |
| 7,061,168 B2 | 6/2006 | Schmidt | |
| 7,073,579 B2 | 7/2006 | Ringgenberg et al. | |
| 7,086,463 B2 | 8/2006 | Ringgenberg et al. | |
| 7,095,012 B2 | 8/2006 | Fujisawa et al. | |
| 7,195,731 B2 | 3/2007 | Jones | |
| 7,245,382 B2 | 7/2007 | Ronnekleiv | |
| 7,248,370 B2 | 7/2007 | Jones | |
| 7,251,037 B2 | 7/2007 | Jones | |
| 7,251,565 B2 | 7/2007 | Storm et al. | |
| 7,280,214 B2 | 10/2007 | DiFoggio et al. | |
| 7,293,613 B2 | 11/2007 | Goldberg et al. | |
| 7,315,377 B2 | 1/2008 | Holland et al. | |
| 7,337,660 B2 | 3/2008 | Ibrahim et al. | |
| 7,347,267 B2 | 3/2008 | Morys et al. | |
| 7,362,422 B2 | 4/2008 | DiFoggio et al. | |
| 7,377,217 B2 | 5/2008 | Swanson | |
| 7,423,258 B2 | 9/2008 | DiFoggio et al. | |
| 7,490,428 B2 | 2/2009 | Morys | |
| 7,490,664 B2 | 2/2009 | Skinner et al. | |
| 7,508,506 B2 * | 3/2009 | Christian et al. | 356/319 |
| 7,511,819 B2 | 3/2009 | DiFoggio | |
| 7,511,823 B2 | 3/2009 | Schultz et al. | |
| 7,532,129 B2 | 5/2009 | Radzinski | |
| 7,571,644 B2 | 8/2009 | Ibrahim et al. | |
| 7,579,841 B2 | 8/2009 | San Martin et al. | |
| 7,581,435 B2 | 9/2009 | Pelletier | |
| 7,696,756 B2 | 4/2010 | Morys et al. | |
| 7,697,141 B2 | 4/2010 | Jones et al. | |
| 7,762,131 B2 | 7/2010 | Ibrahim et al. | |
| 7,775,276 B2 | 8/2010 | Pelletier et al. | |
| 7,784,350 B2 | 8/2010 | Pelletier | |
| 7,800,513 B2 | 9/2010 | Morys | |
| 7,866,387 B2 | 1/2011 | Van Zuilekom et al. | |
| 7,938,175 B2 | 5/2011 | Skinner et al. | |
| 7,958,936 B2 | 6/2011 | McGregor et al. | |
| 7,976,780 B2 | 7/2011 | Elrod et al. | |
| 8,037,935 B2 | 10/2011 | Pelletier | |
| 8,212,568 B2 | 7/2012 | Morys et al. | |
| 8,237,920 B2 | 8/2012 | Jones et al. | |
| 2001/0016562 A1 | 8/2001 | Muir et al. | |
| 2003/0048441 A1 | 3/2003 | Manning | |
| 2003/0048450 A1 * | 3/2003 | Pope et al. | 356/435 |
| 2004/0023407 A1 * | 2/2004 | Casal et al. | 436/171 |
| 2004/0069942 A1 | 4/2004 | Fujisawa et al. | |
| 2004/0152028 A1 | 8/2004 | Singh et al. | |
| 2004/0159002 A1 | 8/2004 | Carlucci et al. | |
| 2004/0164237 A1 | 8/2004 | Jones et al. | |
| 2005/0005694 A1 | 1/2005 | Jones et al. | |
| 2005/0007583 A1 | 1/2005 | DiFoggio | |
| 2005/0019955 A1 | 1/2005 | Dahl et al. | |
| 2005/0099618 A1 | 5/2005 | DiFoggio et al. | |
| 2005/0213313 A1 | 9/2005 | Baumberg et al. | |
| 2006/0052963 A1 | 3/2006 | Shkarlet | |
| 2006/0142955 A1 | 6/2006 | Jones et al. | |
| 2007/0035736 A1 | 2/2007 | Vannuffelen et al. | |
| 2007/0103162 A1 | 5/2007 | Morys et al. | |
| 2007/0259433 A1 | 11/2007 | Jones et al. | |
| 2008/0099241 A1 | 5/2008 | Ibrahim et al. | |
| 2008/0125335 A1 | 5/2008 | Bhavsar | |
| 2008/0202747 A1 | 8/2008 | Gleitman et al. | |
| 2008/0297808 A1 | 12/2008 | Riza et al. | |
| 2009/0095529 A1 | 4/2009 | Rezgui et al. | |
| 2009/0107667 A1 | 4/2009 | Mullins et al. | |
| 2009/0120637 A1 | 5/2009 | Kirkwood et al. | |
| 2009/0151939 A1 | 6/2009 | Bailey et al. | |
| 2009/0180101 A1 * | 7/2009 | Csutak | 356/70 |
| 2009/0199630 A1 * | 8/2009 | DiFoggio et al. | 73/152.28 |
| 2009/0288820 A1 | 11/2009 | Barron et al. | |
| 2010/0148787 A1 | 6/2010 | Morys et al. | |
| 2010/0153048 A1 | 6/2010 | Myrick et al. | |
| 2010/0231225 A1 | 9/2010 | Morys et al. | |
| 2010/0245096 A1 | 9/2010 | Jones et al. | |
| 2010/0265094 A1 | 10/2010 | Zannoni et al. | |
| 2011/0023583 A1 | 2/2011 | Jones et al. | |
| 2011/0023594 A1 | 2/2011 | Pelletier et al. | |
| 2011/0031972 A1 | 2/2011 | Pelletier et al. | |
| 2011/0181870 A1 | 7/2011 | Penney et al. | |
| 2011/0218736 A1 | 9/2011 | Pelletier et al. | |
| 2011/0251794 A1 | 10/2011 | Bittar et al. | |

(56) References Cited

U.S. PATENT DOCUMENTS

| | | | |
|---|---|---|---|
| 2012/0018152 | A1 | 1/2012 | Zuilekom et al. |
| 2012/0018167 | A1 | 1/2012 | Konopczynski et al. |
| 2012/0084021 | A1 | 4/2012 | Jones et al. |
| 2012/0150451 | A1 | 6/2012 | Skinner et al. |
| 2012/0160018 | A1 | 6/2012 | Jones et al. |
| 2012/0211650 | A1 | 8/2012 | Jones et al. |
| 2012/0223221 | A1 | 9/2012 | Jones et al. |
| 2012/0232707 | A1 | 9/2012 | Jones et al. |
| 2012/0250017 | A1 | 10/2012 | Morys et al. |
| 2013/0068940 | A1 | 3/2013 | Jones et al. |
| 2013/0109100 | A1 | 5/2013 | Sarkar et al. |

FOREIGN PATENT DOCUMENTS

| | | |
|---|---|---|
| GB | 310895 | 10/1930 |
| GB | 1088268 | 10/1967 |
| GB | 2064217 | 6/1981 |
| GB | 2441069 | 2/2008 |
| GB | 2493652 | 2/2013 |
| JP | H0227686 | 1/1990 |
| JP | 2003157807 | 5/2003 |
| WO | WO-2004003984 | 1/2004 |
| WO | WO-2011/063086 | 5/2011 |
| WO | WO-2011/078869 | 6/2011 |
| WO | WO-2011/153190 | 12/2011 |
| WO | WO-2011/159289 | 12/2011 |
| WO | WO-2011/159294 | 12/2011 |
| WO | WO-2012/161693 | 11/2012 |

OTHER PUBLICATIONS

Balasubramanian, Gopalakrishnan et al., "Nanoscale Imaging Magnetometry with Diamond Spins under Ambient Conditions", Nature, vol. 455, Oct. 2, 2008, pp. 648-651.

Bittar, Michael S., et al., "A 3D Borehole Imager", U.S. Appl. No. 13/061,759, filed Mar. 2, 2011, 15 pgs.

Bleier, Z et al., "A Monolithic Interferometer for FT-IR Spectroscopy", Spectroscopy, 13 (10), pp. 46-49.

Boudou, J.P. et al., "High Yield Fabrication of Fluorescent Nanodiamonds", Nanotechnology v20 n23, Jun. 10, 2009, 11 pgs.

Dumeige, Y. et al., "Photo-Induced Creation of Nitrogen-Related Color Centers in Diamond Nanocrystals Under Femtosecond Illumination", Elsevier, www.elsevier.com/locate/jlumin, Journal of Luminescence 109 (2004), pp. 61-67.

Faklaris, Orestis et al., "Comparison of the Photoluminescence Properties of Semiconductor Quantum Dots and Non-Blinking Diamond Nanoparticles. Observation of the Diffusion of Diamond Nanoparticlesin Living Cells", J. European Optical Society, v4, 2009, 8 pgs.

Florescu, Marian et al., "Improving Solar Cell Efficiency Using Photonic Band-Gap Materials", ScienceDirect.com, (Jun. 29, 2007),1599-1610.

ICX Photonics, "markIR Infrared Emitters", icxphotonics.com, ICx Photonics,pp. 1-2.

Jones, Christopher M., et al., "Spectroscopic Nanosensor Logging Systems and Methods", PCT Appl No. PCT/US11/038693; filed Jun. 1, 2011, 16 pgs.

Lee, Seung W., et al., "A Soluble Photoreactive Polyimide Bearing the Coumarin Chromophore in the Side Group: Photoreaction, Photoinduced Molecular Reorientation, and Liquid-Crystal Alignability in Thin Films", Langmuir 19 (24) 2003, pp. 10381-10389.

PCT International Search Report and Written Opinion, dated Aug. 24, 2010, Appl No. PCT/US10/038747 , "Downhole Sources Having Enhanced IR Emission", filed Jun. 16, 2010, 8 pgs.

PCT Int'l Search Report and Written Opinion, dated Jun. 3, 2010, Appl No. PCT/US09/069492, Interferometry-Based Downhole Analysis Tool, filed Dec. 23, 2009, 8 pgs.

Pelletier, Michael T., et al., "Downhole Sources Having Enhanced IR Emission", PCT Appl No. PCT/US10/038747 , "Downhole Sources Having Enhanced IR Emission", filed Jun. 16, 2010, Appl No. PCT/US10/038747 , "Downhole Sources Having Enhanced IR Emission", filed Jun. 16, 2010, 22 pgs.

Rabeau, J. R., et al., "Single Nitrogen Vacancy Centers in Chemical Vapor Deposited Diamond Nanocrystals", Nano Letters, v7 n11 p. 3433-3437, 2007, Macquarie University, New South Wales 2109, Australia., pp. 1-20.

Simons, J. K., et al., "X-ray Energy Dependent Photochemestry of the Adamantane (C10H16)/Si(111)-7×7 Surface", American Vacuum Society, J. Vac Sci. Technol. A 11(4) Jul./Aug. 1993, pp. 2244-2249.

Sonnefraud, Yannick et al., "25-nm Diamond Cyrstals Hosting Single NV Color Centers Sorted by Photon-Correlation Near-field Microscopy", Optics Letters, vol. 33, Issue 6, 2008, pp. 611-613.

Tank, V. "Remote Detection and Quantification of Hot Molecular Combustion Products—Experimental Instrumentation and Determination of Optimal Infrared Spectral Micro Windows", Journal of Molecular Structure, vol. 744-747, 3, pp. 235-242.

Tisler, Julia et al., "Fluorescence and Spin Properties of Defects in Single Digit Nanodiamonds", American Chemical Society, ACS Nano v3 n7 p. 1959-1965, 2009, pp. 1959-1965.

Van Der Sar, T. et al., "Nanopositioning of a Diamond Nanocrystal Containing a Single NV Defect Center", Applied Physics Letters v94 n17, 2009, 3 pgs.

Zhang, Wei et al., "Method to Increase the Number of Filters per Optical Path in a Downhole Spectrometer", PCT Appl No. PCT/US11/03655, filed May 24, 2011, 12 pgs.

AU First Examination Report, dated Jun. 24, 2013, Appl No. 2010355321, "Downhole Sources Having Enhanced IR Emission", filed Jun. 6, 2010, 3 pgs.

US Non-Final Office Action, dated Jul. 2, 2013, U.S. Appl. No. 13/510,231, "Downhole Sources Having Enhanced IR Emission", filed May 16, 2012, 38 pgs.

PCT International Search Report and Written Opinion, dated Mar. 2, 2011, Appl No. PCT/US2010/057172, "Downhole Optical Radiometry Tool", filed Nov. 18, 2010, 13 pgs.

PCT International Search Report and Written Opinion, dated Sep. 16, 2011, Appl No. PCT/US2011/038693, "Spectroscopic Nanosensor Logging Systems and Methods", filed Jun. 1, 2011, 10 pgs.

Alaskar, Mohammed, et al., "In-Situ Multifunction Nanosensors for Fractured Reservoir Characterization", Proceedings, Thirty-fifth Workshop on Geothermal Reservoir Engineering, Stanford University, Stanford, California, Feb. 1-3, 2010, SGP-TR-188., 13 pgs., Retrieved from the Internet <http://ere.stanford.edu/pdf/IGAstandard/SGW/2010/askar.pdf>.

Myrick, M. L., et al., "Application of Multivariate Optical Computing to Simple Near-Infrared Point Measurements", Proceedings of SPIE, vol. 4574, (2002), pp. 208-215.

Zhang, Wei et al., Appl No. PCT/US2011/037662, "Downhole Optical Fluid Analyzer Having Intermittently Driven Filter Wheel", filed May 24, 2011, 15 pgs.

PCT International Preliminary Report on Patentability, dated May 31, 2012, Appl No. PCT/US2010/057172, "Downhole Optical Radiometry Tool", filed Nov. 18, 2010, 8 pgs.

First Australian Examination Report, dated Jun. 25, 2012, Appl No. 2009356978, "Interferometry-Based Downhole Analysis Tool", filed Dec. 23, 2009, 4 pgs.

PCT International Preliminary Report on Patentability, dated Jul. 5, 2012, Appl No. PCT/US2009/069492, "Interferometry-Based Downhole Analysis Tool", filed Dec. 23, 2009, 7 pgs.

International Search Report and Written Opinion, dated Oct. 28, 2011, Appl No. PCT/US/2011/027655, "Method to Increase the Number of Filters per Optical Path in a Downhole Spectrometer", filed May 24, 2011, 10 pgs.

Morys, Marian, et al., "Nuclear Magnetic Resonance Logging Tool Having an Array of Antennas", Appl No. PCT/US2010/038844, filed Jun. 16, 2010, 30 pgs.

PCT International Preliminary Report on Patentability, dated Jan. 3, 2013, Appl No. PCT/US2010/038747, "Downhole Sources Having Enhanced IR Emission", filed Jun. 16, 2010, 7pgs.

PCT International Preliminary Report on Patentability, dated Dec. 13, 2012, Appl No. PCT/US2011/038693, "Spectroscopic Nanosensor Logging Systems and Methods", filed Jun. 1, 2011, 9 pgs.

First Chinese Office Action, dated Feb. 5, 2013, Appl No. 200980157701.3, "Interferometry-Based Downhole Analysis Tool", filed Dec. 23, 2009, 13 pgs.

(56) References Cited

OTHER PUBLICATIONS

Canadian Examiner Letter, dated Oct. 24, 2012, Appl No. 2,756,285, "Interferometry-Based Downhole Analysis Tool", filed Dec. 23, 2009, 2 pgs.

Supplementary European Search Report, dated Sep. 2, 2013, Appl No. 10853352.2, "Downhole Sources Having Enhanced IR Emissions", filed Jun. 16, 2010, 13 pgs.

CA Examiner'S Letter, dated Jul. 31, 2013, Appl No. 2,781,331, "Downhole Sources Having Enhanced IR Emission", filed May 16, 2012, 6 pgs.

European Search Report, dated Dec. 12, 2013, Appl No. 09852686.6, "Interferometry-Based Downhole Analysis Tool", filed Dec. 23, 2009, 7 pgs.

US Non-Final Office Action, dated Jan. 28, 2014, U.S. Appl. No. 13/636,294, "Spectroscopic Nanosensor Logging Systems and Methods," filed Sep. 20, 2012, 28 pgs.

Downhole Sources Having Enhanced IR Emission, dated Feb. 4, 2014, Appl No. 2014200604, "Downhole Sources Having Enhanced IR Emission," filed Jan. 4, 2014, 35 pgs.

US Final Office Action, dated Apr. 17, 2014, Appl No. 2013/510,231Downhole Sources Having Enhanced IR Emission, filed May 16, 2012, 18 pgs.

US Non-Final Office Action, dated Apr. 25, 2014, U.S. Appl. No. 13/502,805, "Downhole Optical Radiometry Tool," filed Apr. 19, 2012, 19 pgs.

US Final Office Action, dated May 15, 2014, U.S. Appl. No. 13/636,294, "Spectroscopic Nanosensor Logging Systems and Methods," filed Sep. 20, 2012, 25 pgs.

\* cited by examiner

INTERFEROMETRY-BASED DOWNHOLE ANALYSIS TOOL

BACKGROUND

Modern oil field operators demand access to a great quantity of information regarding the parameters and conditions encountered downhole. Such information typically includes characteristics of the earth formations traversed by the borehole and data relating to the size and configuration of the borehole itself. The collection of information relating to conditions downhole, which commonly is referred to as "logging," can be performed by several methods including wireline logging, "logging while drilling" (LWD), and tubing-conveyed logging.

In wireline logging, a probe or "sonde" is lowered into the borehole after some or all of the well has been drilled. The sonde hangs at the end of a long cable or "wireline" that provides mechanical support to the sonde and also provides an electrical connection between the sonde and electrical equipment located at the surface of the well. In accordance with existing logging techniques, various parameters of the earth's formations are measured and correlated with the position of the sonde in the borehole as the sonde is pulled uphole.

In LWD, the drilling assembly includes sensing instruments that measure various parameters as the formation is being penetrated, thereby enabling measurements of the formation while it is less affected by fluid invasion. While LWD measurements are desirable, drilling operations create an environment that is generally hostile to electronic instrumentation, telemetry, and sensor operations.

Tubing-conveyed logging, like wireline logging, is performed in an existing borehole. Unlike wireline logging, tubing-conveyed logging enables a logging tool to travel where a wireline-suspended tool cannot, e.g., in a horizontal or ascending borehole. Tubing-conveyed logging tools typically suffer from restricted communications bandwidths, meaning that acquired data is generally stored in memory and downloaded from the tool when the tool returns to the surface.

In these and other logging environments, measured parameters are usually recorded and displayed in the form of a log, i.e., a two-dimensional graph showing the measured parameter as a function of tool position or depth. In addition to making parameter measurements as a function of depth, some logging tools also provide parameter measurements as a function of azimuth. Such tool measurements have often been displayed as two-dimensional images of the borehole wall, with one dimension representing tool position or depth, the other dimension representing azimuthal orientation, and the pixel intensity or color representing the parameter value.

Once a borehole has been drilled, operators often wish to perform downhole formation testing before finalizing a completion and production strategy. Fluid sampling tools enable operators to draw fluid samples directly from the borehole wall and measure contamination levels, compositions, and phases, usually based on the properties (e.g., optical properties, electrical properties, density, NMR, and PVT properties) of the materials drawn into the sample chamber.

DESCRIPTION OF THE DRAWINGS

A better understanding of the various disclosed embodiments can be obtained when the following detailed description is considered in conjunction with the attached drawings, in which.

Figure 1:
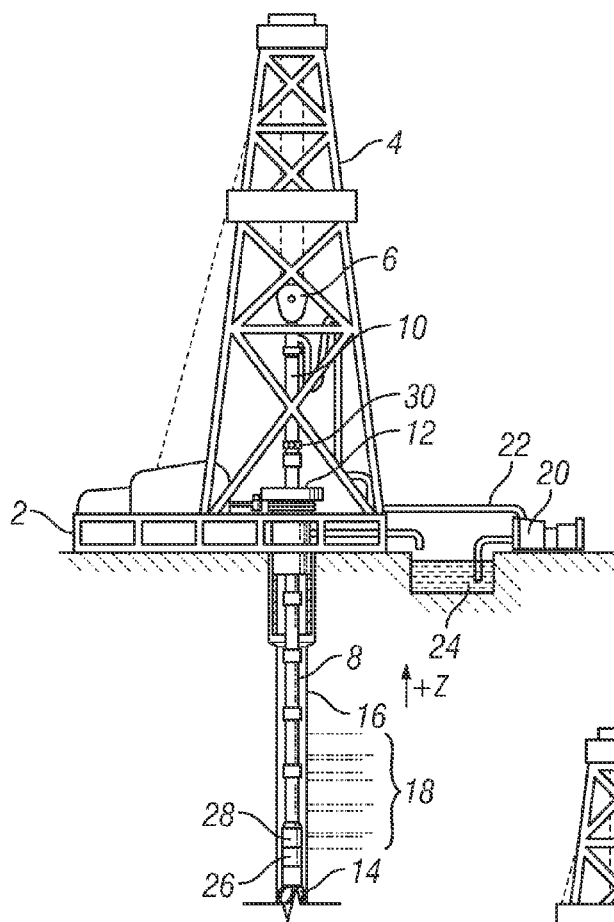
FIG. 1 shows an illustrative environment for logging while drilling ("LWD")

While the invention is susceptible to various modifications and alternative forms, specific embodiments thereof are shown by way of example in the drawings and will herein be described in detail. It should be understood, however, that the drawings and detailed description thereto are not intended to limit the disclosure, but on the contrary, the intention is to cover all modifications, equivalents and alternatives falling within the plain-language scope of the claims.

DETAILED DESCRIPTION

Accordingly, there are disclosed herein various systems and methods for performing optical analysis downhole with an interferogram (a pattern of interference created by superposition of light waves). The interferogram is produced by introducing an interferometer into the light path, with the two arms of the interferometer having a propagation time difference that varies as a function of time. Before or after the interferometer, the light encounters a material to be analyzed, such as a fluid sample from the formation, a borehole fluid sample, a core sample, or a portion of the borehole wall. The encounter can take various forms, including transmission/attenuation through the sample, reflection off the sample, attenuated total reflectance (evanescent wave), scattering from the sample, and fluorescence excitation. In any event, the spectral characteristics of the material are imprinted on the light beam and can be readily analyzed by processing electronics that perform a Fourier Transform to obtain the spectrum or that enable a comparison with one or more templates. An interferometer designed to perform well in the hostile environments downhole is expected to enable laboratory-quality measurements.

The disclosed systems and methods are best understood in the context of the larger systems in which they operate. FIG. 1 shows an illustrative logging while drilling (LWD) environment. A drilling platform 2 supports a derrick 4 having a traveling block 6 for raising and lowering a drill string 8. A kelly 10 supports the drill string 8 as it is lowered through a rotary table 12. A drill bit 14 is driven by a downhole motor and/or rotation of the drill string 8. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus around drill string 8, and into a retention pit 24. The drilling fluid transports cuttings from the borehole into the pit 24 and aids in maintaining the borehole integrity.

A LWD tool 26 is integrated into the bottom-hole assembly near the bit 14. As the bit extends the borehole through the formations, logging tool 26 collects measurements relating to various formation properties as well as the tool orientation and various other drilling conditions. The logging tool 26 may take the form of a drill collar, i.e., a thick-walled tubular that provides weight and rigidity to aid the drilling process. As explained further below, tool assembly 26 includes a optical fluid analysis tool that monitors wellbore fluid properties. A telemetry sub 28 may be included to transfer measurement data to a surface receiver 30 and to receive commands from the surface. In some embodiments, the telemetry sub 28 does not communicate with the surface, but rather stores logging data for later retrieval at the surface when the logging assembly is recovered.

Figure 2:
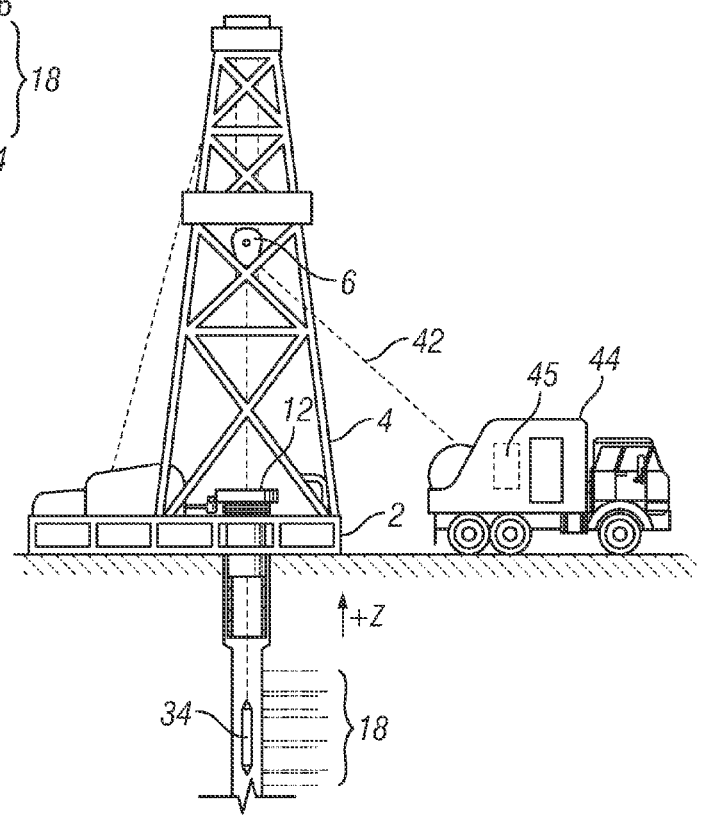
FIG. 2 shows an illustrative environment for wireline logging.

At various times during the drilling process, the drill string 8 may be removed from the borehole as shown in FIG. 2. Once the drill string has been removed, logging operations can be conducted using a wireline logging tool 34, i.e., a sensing instrument sonde suspended by a cable 42 having conductors for transporting power to the tool and telemetry from the tool to the surface. A wireline logging tool 34 may have pads and/or centralizing springs to maintain the tool near the axis of the borehole as the tool is pulled uphole. As explained further below, tool 34 can include a formation fluid sampler that extends a probe against a borehole wall to draw fluids into a sample analysis chamber. A surface logging facility 44 collects measurements from the logging tool 34, and includes a computer system 45 for processing and storing the measurements gathered by the logging tool.

Figure 3:
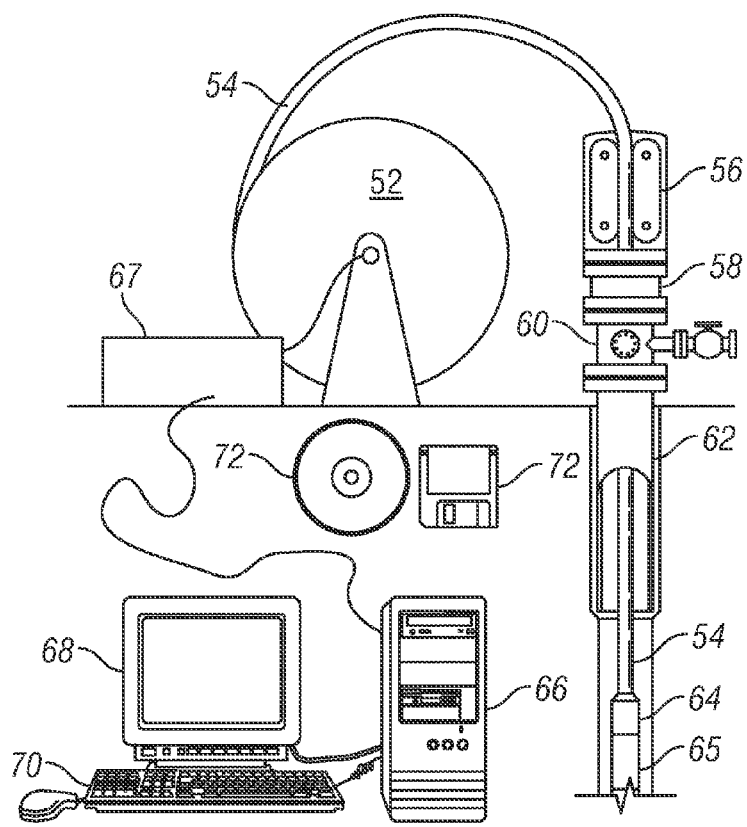
FIG. 3 shows an illustrative environment for tubing-conveyed logging.

An alternative logging technique is logging with coil tubing. FIG. 3 shows an illustrative coil tubing-conveyed logging system in which coil tubing 54 is pulled from a spool 52 by a tubing injector 56 and injected into a well through a packer 58 and a blowout preventer 60 into the well 62. (It is also possible to perform drilling in this manner by driving the drill bit with a downhole motor.) In the well, a supervisory sub 64 and one or more logging tools 65 are coupled to the coil tubing 54 and optionally configured to communicate to a surface computer system 66 via information conduits or other telemetry channels. An uphole interface 67 may be provided to exchange communications with the supervisory sub and receive data to be conveyed to the surface computer system 66.

Surface computer system 66 is configured to communicate with supervisory sub 64 during the logging process or alternatively configured to download data from the supervisory sub after the tool assembly is retrieved. Surface computer system 66 is preferably configured by software (shown in FIG. 3 in the form of removable storage media 72) to process the logging tool measurements (including the interferogram measurements described further below). System 66 includes a display device 68 and a user-input device 70 to enable a human operator to interact with the system software 72.

In each of the foregoing logging environments, the logging tool assemblies preferably include a navigational sensor package that includes directional sensors for determining the inclination angle, the horizontal angle, and the rotational angle (a.k.a. "tool face angle") of the bottom hole assembly. As is commonly defined in the art, the inclination angle is the deviation from vertically downward, the horizontal angle is the angle in a horizontal plane from true North, and the tool face angle is the orientation (rotational about the tool axis) angle from the high side of the wellbore. In accordance with known techniques, wellbore directional measurements can be made as follows: a three axis accelerometer measures the earth's gravitational field vector relative to the tool axis and a point on the circumference of the tool called the "tool face scribe line". (The tool face scribe line is typically drawn on the tool surface as a line parallel to the tool axis.) From this measurement, the inclination and tool face angle of the logging assembly can be determined. Additionally, a three axis magnetometer measures the earth's magnetic field vector in a similar manner. From the combined magnetometer and accelerometer data, the horizontal angle of the logging assembly can be determined.

Figure 4:
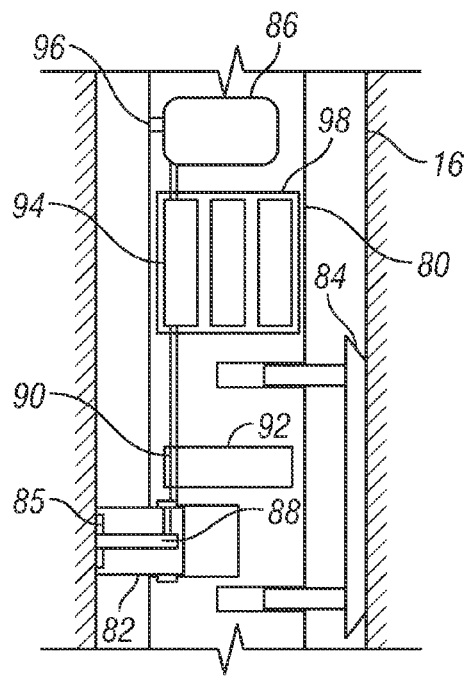
FIG. 4 shows an illustrative formation fluid sampling tool.

FIG. 4 shows an illustrative formation fluid sampler tool 80. Tool 80 can be a drill collar, a coil tubing joint, or a drilling tubular, but most commonly it is expected to be part of a wireline sonde. Tool 80 extends a probe 82 and a foot 84 to contact the borehole wall 16, typically driving them outward from the tool body using hydraulic pressure. The probe 82 and foot 84 cooperate to seat the probe firmly against the borehole wall and establish a seal that keeps borehole fluids from being drawn into the sampling tool. To improve the seal, the wall-contacting face of the probe includes an elastomeric material 85 that conforms to the borehole wall. A pump 86 draws down the pressure, prompting fluid to flow from the formation through a probe channel 88, a sample chamber 90 in fluid analyzer 92, and a sample collection chamber 94. The pump 86 exhausts fluid into the borehole through a port 96 and continues pumping until the sampling process is completed. Typically, the sampling process continues until the tool determines that the sample collection chamber 94 is full and any contaminants have been exhausted. Thereafter the sample collection chamber is sealed and the probe and foot are retracted. If desired, the tool can repeat the process at different positions within the borehole. Sample collection chamber 94 may be one of many such sample collection chambers in a cassette mechanism 98, enabling the tool to return many fluid samples to the surface.

Figure 5:
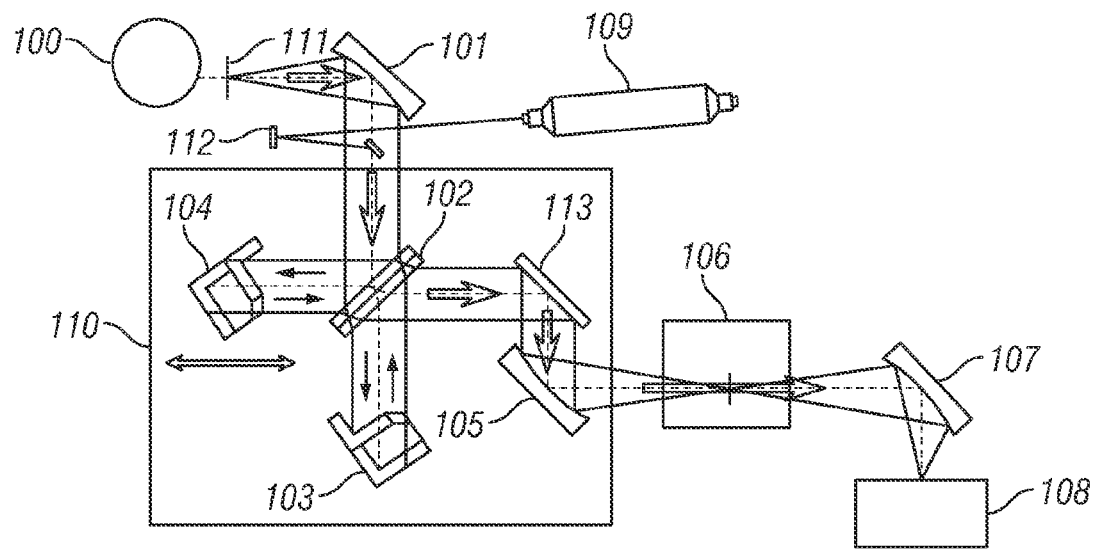
FIG. 5 shows an illustrative interferometer-based fluid analyzer.

FIG. 5 shows an illustrative interferometer-based fluid analyzer. A broadband light source 100 radiates light through an optional aperture 111. For the purposes of this disclosure, the term "broadband" is used to distinguish from narrowband sources that provide only isolated peaks in their spectrum. The broadband sources contemplated for use downhole have continuous spectrums in the range of 200-400 nm (for UV absorption and fluorescence spectroscopy), 1500-2300 nm (for special purpose spectroscopy, e.g. GOR determination), and 400-6000 nm (for general purpose VIS-IR spectroscopy). These examples are merely illustrative and not limiting. One readily available source suitable for this purpose is a tungsten-halogen incandescent source with a quartz envelope, generating light across the 300-3000 nm range.

A collimation mirror 101 parallelizes the light rays from the light source 100 and directs the light to a beam splitter 102 in an interferometer 110. The beam splitter is directs half of the light to a fixed mirror 103 and the other half to a movable mirror 104. (Mirrors 103 and 104 are shown as retroreflectors, which exhibit improved tolerance for misalignment errors than do flat mirrors.) The mirrors reflect the light back to the beam splitter 102. At this point, the beams have traveled path lengths having a difference that depends on the position of the movable mirror 104. Movable mirror 104 oscillates back and forth, causing the combined beam leaving the beam splitter to suffer interference in a manner that makes the different frequency components of the light beam undergo intensity oscillations at rates that are related to their frequencies. This combined beam is herein termed a "spectralized" beam, because it makes the spectral composition of the beam measurable from the time variation of its intensity. (In the literature, this spectralized beam is sometimes referred to as an "interferogram".)

As it exits the interferometer 110, the spectralized beam travels from the beam splitter 102 (via an intermediate mirror 113) to a focusing mirror 105. The focusing mirror 105 focuses the light at a point in a sample chamber 106, after which a second focusing mirror 107 directs the light onto a detector 108. The detector 108 measures the time variation of the incident light intensity. In some embodiments, the electronics process the measured time variation, determining a Fourier Transform that reveals the transmission spectrum of the material in the sample chamber 106. Note, however, that the Fourier Transform is not obligatory. In some embodiments, the electronics operate on the interferogram in the time-domain to measure characteristics of the material in the sample chamber.

The rate of intensity variation for each of the frequency components depends on the speed of the movable mirror 104. To compensate for variations in this speed, the processing electronics can track the position of the movable mirror. Alternatively, a narrowband light beam can be added to the broadband light beam. In FIG. 5, this is done by passing light from a laser 109 (or other gas discharge source having well-defined spectral peaks) through a hole in collimating mirror 101 or being inserted via one or more mirrors 112. The oscillations in the interferogram from the laser source provide means for accurate position tracking of the moving mirror. Well-defined peaks in the gas discharge spectrum similarly enable the processing electronics to detect and compensate minor irregularities in the motion of mirror 104 and/or provide diagnostic measurements of the system performance.

Figure 6:
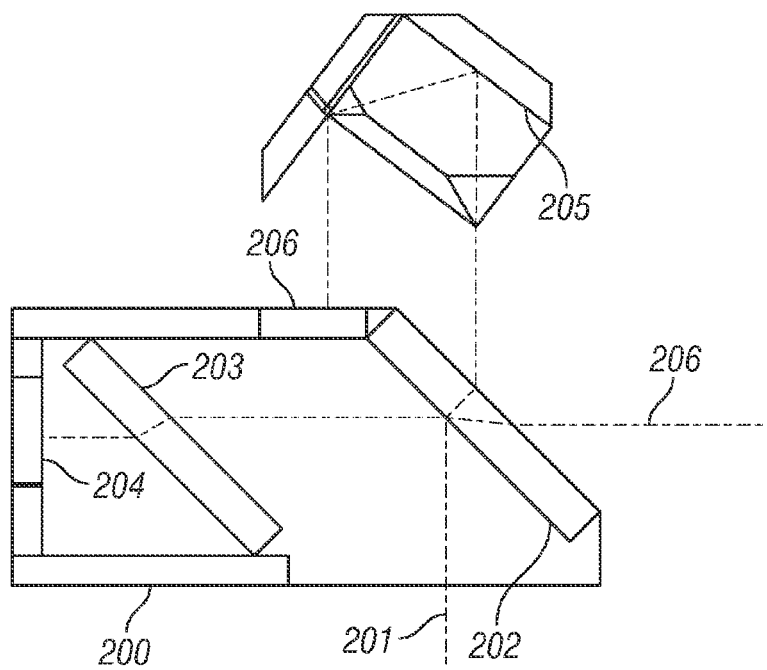
FIG. 6 shows an illustrative interferometer with an integrated ("monolithic") light path component.

FIG. 6 shows an illustrative interferometer with an integrated ("monolithic") light path component. The integrated component provides reduced sensitivity to temperature changes, pressure changes, vibrations, and shock. A solid block of transparent material (e.g., quartz, sapphire, zinc selenide) is used as the body of the integrated component. Mirrors and a beam splitter, also made of the same material, are fused or otherwise attached to this body. An optional compensator can also be fused into place.

The input light beam 201 enters through a polished surface of the body and impinges on a beam splitter 202. Half of the light is reflected (via the optional compensator 203) off of a fixed mirror 204, from which it returns to the beam splitter 202. The other half of the light travels outside the integrated component, via a retroreflector 205, to reflect off of a fixed mirror 206 attached to the body of the integrated component. From the fixed mirror 206, the light returns (again via the retroreflector) to the beam splitter 202, where it combines with light from the other path to form an output beam 206.

As before, motion of the movable retroreflector causes the output beam to be spectralized. The movable element can be reciprocated by various mechanisms. In some embodiments, the movable element is mounted on a spring and driven with an inductive field acting on a magnet. In other embodiments, a piezoelectric element is used to convert voltage into axial motion. Similarly, a magnetic field can drive a magnetorestrictive element, The speed of the movable retroreflector can be tracked directly or measured using a reference light beam injected as before. Although the monolithic construction offers improved stability, the speed of the retroreflector can still be affected by vibration, shock, or imperfections in the drivers. A rotary motion can often be more precisely controlled and suffer less sensitivity to vibration or shock.

Figure 7:
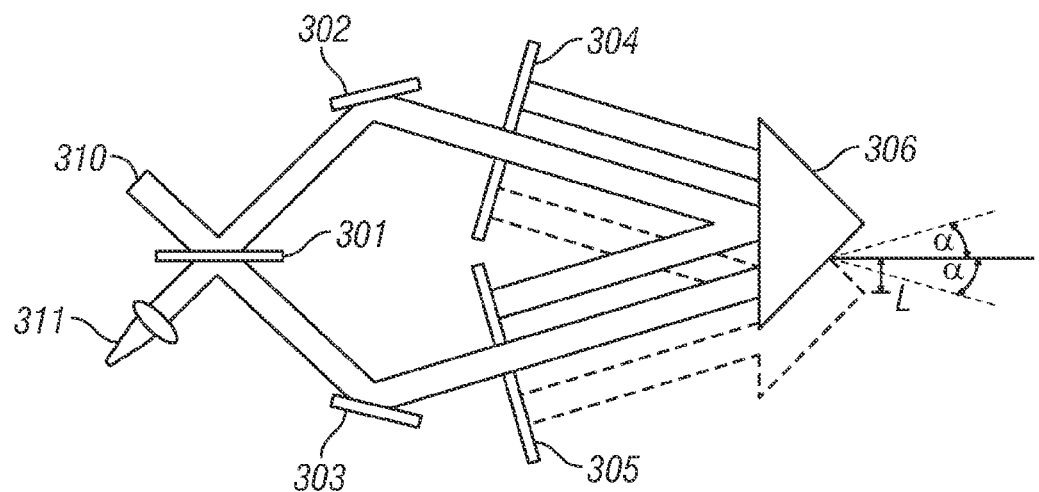
FIG. 7 shows an illustrative interferometer employing a spinning retroreflector.

Accordingly, FIG. 7 shows an illustrative interferometer employing a spinning retroreflector. Light from a source 310 strikes a beam splitter 301, which routes half of the light to a spinning retroreflector 306 via a first fixed mirror 302 and a mirror with a hole 304. (FIG. 7 actually shows two positions of the retroreflector—for the moment we assume the retroreflector is in the upper position shown with dark shading.) The retroreflector 306 bounces this light off of the mirror with a hole 304, which returns the light back along this path to the beam splitter 301. The other half of the light is similarly routed to the spinning retroreflector 306 via a second fixed mirror 303 and a second mirror with a hole 305. The retroreflector bounces the light off of the mirror with a hole 305, which returns the light along this path to the beam splitter 301. The combined light from both paths exits the interferometer at 311 to illuminate the sample and be measured by the detector.

This configuration makes use of two properties of the corner reflector. First—corner reflectors are a type of retroreflector, meaning that incident light is reflected in a direction parallel to the incoming light, regardless of the direction of incidence. Second—when the light strikes the retroreflector from an off-axis direction, the distance traveled by the light varies based on the light's offset distance from the axis in the base plane. (The base plane includes the apex of the corner reflector and is oriented perpendicular to the axis of the corner reflector.) Thus, when a corner reflector spins around an offset axis, the light path of light striking the corner reflector from an angle undergoes a periodic oscillation in length. The light path for light striking from an opposite angle as shown in FIG. 7 undergoes a periodic oscillation that is 180° out of phase with the oscillation of the first light path, thereby doubling the difference in lengths of the two light paths.

The use of a spinning corner reflector 306 provides improved performance because rotary motion can be precisely controlled even in the presence of vibration, and the position of a rotating object can be easily measured, e.g., using a rotary position encoder. With the ability to track the position of the moving mirror, the need for a reference light beam is eliminated.

Figure 8:
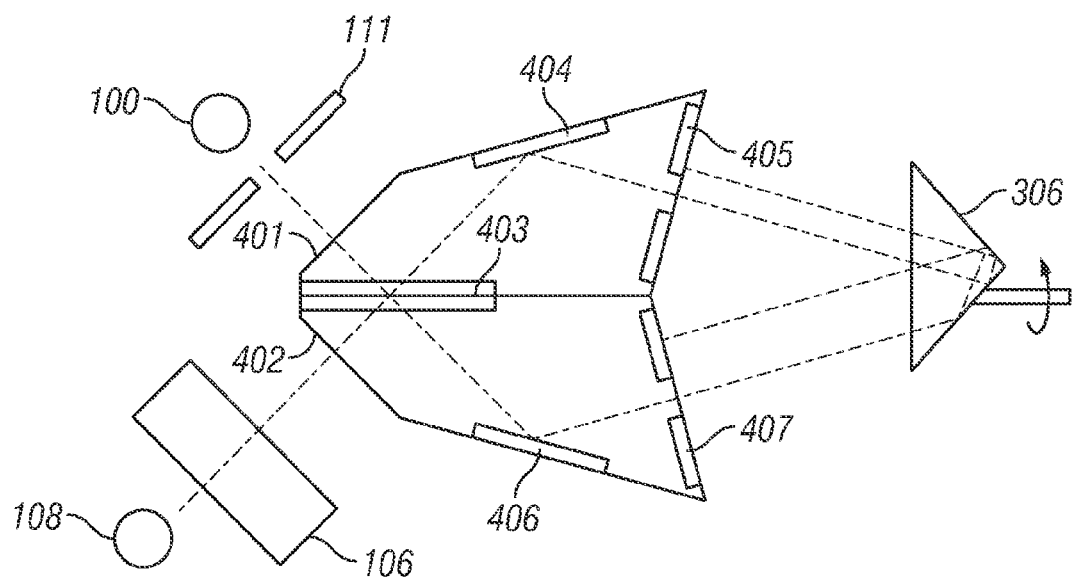
FIG. 8 shows a second illustrative interferometer-based fluid analyzer.

FIG. 8 shows an illustrative interferometer-based fluid analyzer that combines a spinning corner reflector with an integrated light path component. In FIG. 8, two integrated components 401 and 402 can be manufactured separately and then fused to form a single component. The combined component includes a beam splitter 403, two fixed mirrors 404, 406, and two fixed mirrors with a central hole 405, 407. It operates similarly to the embodiment of FIG. 7, with a corner reflector spinning on an offset axis to provide a periodically varying difference between the lengths of the two light paths in the interferometer, thereby spectralizing the broadband light passing from the interferometer to the sample cell 106 and thence to the detector 108. In the illustrated system, the light path passes through the sample chamber 106 after the interferometer. However, the light path could equally well pass through the sample chamber 106 prior to entering the interferometer. With the combined features, the illustrated fluid analyzer is expected to provide highly accurate measurements even in the downhole environment.

Note that other techniques for varying light path differences can be employed in place of the spinning corner reflector. Examples include fibers or waveguides with electrically controlled index of refraction or fibers with controlled stretch, e.g., by varying a magnetic field around an optical fiber clad in a magnetostrictive material or mounted on a magnetostrictive member, or by varying an electrical field across a piezoelectric element to achieve the stretch.

Figure 9:
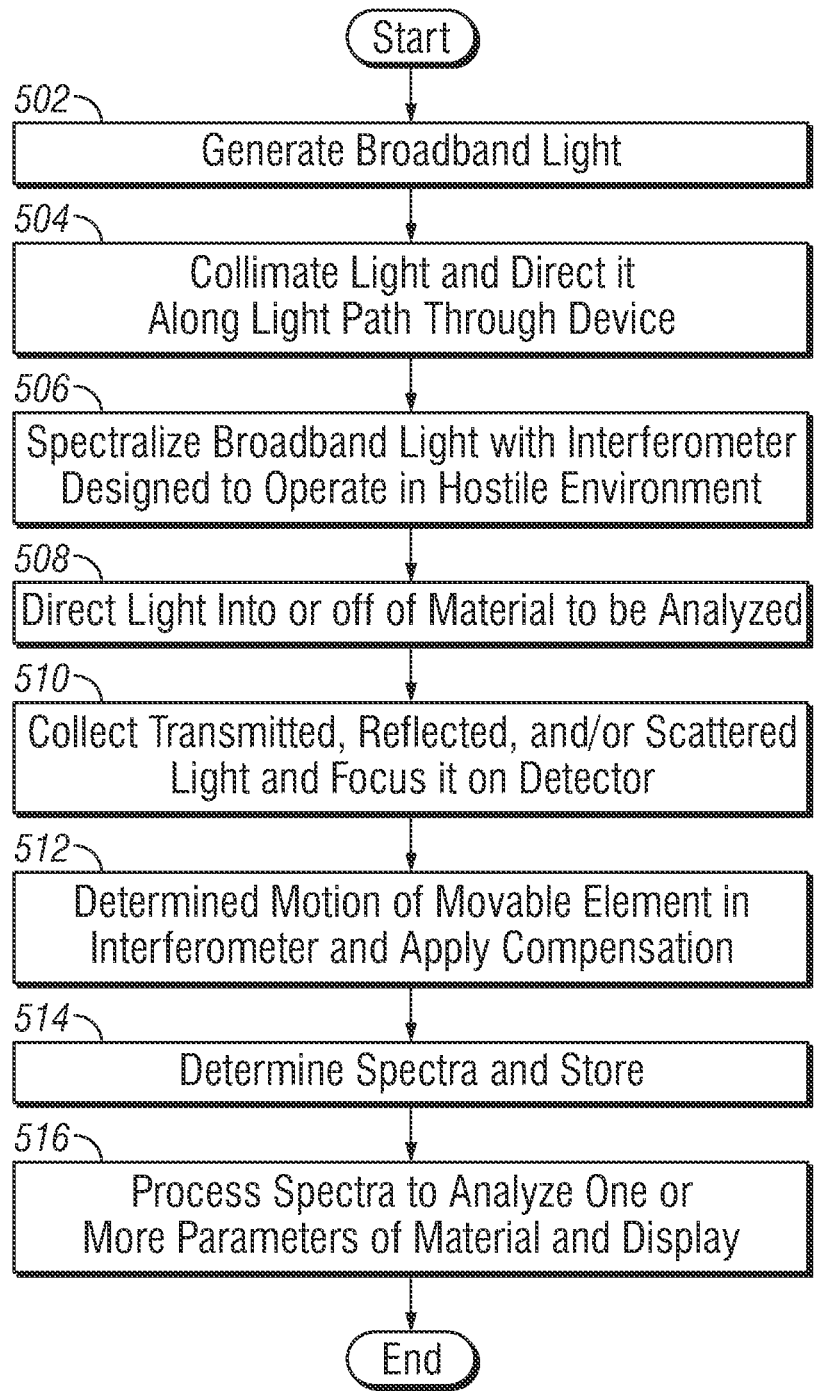
FIG. 9 shows an illustrative interferometer-based analysis method.

FIG. 9 shows an illustrative interferometer-based analysis method. Starting in block 502, the tool generates a broadband light. This can be done in a number of ways including an incandescent light with or without a transparent envelope and/or surrounded by a halogen gas, a broadband fluorescent source, a broadband quantum light source, or a combination of a number of relatively narrowband light sources such as LEDs. In block 504, the tool collimates the light and directs it along the light path through the device using some combination of one or more apertures, reflectors and lenses. Somewhere along the light path, the tool employs an interferometer to spectralize the light beam, as indicated by block 506. The interferometer is designed to operate in the downhole environment, e.g., by employing an integrated light path component that maintains the alignment and spacing of mirrors and beamsplitter(s) over a wide range of temperature, pressure, vibration, and shock conditions. Also, the movable component can take the form of a corner reflector that spins off-axis and is oriented at an angle to the light path, thereby providing an oscillatory variation of the length difference between light paths through the interferometer. The total variation is expected to be in the range between $10^{-4}$ and $10^{-2}$ meter. This mechanism provides for precise control and measurement of the reflector position over a wide range of operating conditions.

Elsewhere along the light path, the tool directs the light to a material that is to be analyzed, as indicated by block 508. The material can take the form of a gas, fluid, or mixed phase flow captured within a sample cell or flowing past a window. Alternatively, the material can be a solid that is visible through a window or aperture, such as a core sample or a portion of the borehole wall adjacent to the tool. In block 510, the tool collects transmitted light, reflected light, scattered light, and/or emitted light or fluorescence from the sample and directs it to a detector of light intensity. The detector can take the form of a photodiode, a thermal detector (including thermopiles and pyroelectric detectors), a Golay cell, or a photoconductive element. Cooling can be employed to improve the signal-to-noise ratio of the detector.

In block 512, the tool tracks the motion of the movable element used in the interferometer (or the variation of some other element used to provide light path length variation) and uses it to determine the appropriate compensation to the measured signal. In block 514, the tool employs a digital signal processor, a general purpose processor, or other processing electronics to digitize the light intensity signal and process it in combination with the motion measurements to determine the spectrum of the light striking the detector. This spectrum is stored in memory for later use, possibly in association with a measurement time and/or tool position.

In block 516, the tool processes the measured interferograms or spectra to analyze one or more parameters of the illuminated material. That parameter is stored, displayed, or used as the basis for a subsequent tool operation (e.g., the decision to stop pumping after the contamination level drops sufficiently. Illustrative analyses include determining contamination levels in a sampled fluid, identifying fluid composition, identifying fluid type, identifying PVT properties, etc. The composition analysis might include determining concentrations of compounds such as $CO_2$, $H_2S$, etc., or determining hydrocarbon fractions of saturated, aromatics, resins, and asphaltenes. Fluid type determination can be finding volume percentages of oil, water, and gas. PVT properties can include bubble point determination, gas/oil ratio, density variation with pressure, etc. Measurements can be communicated to the surface for display to an operator and further processing.

Various processing techniques are known for determining composition or type information from a spectrum of reflected, transmitted, or scattered light. They include Inverse Least Squares Regression and Principal Component Analysis. However, other techniques can also be used, such as operating directly on the time-domain signal rather than converting to the spectral domain. (Correlation of measured interferograms with template interferograms is expected to be an effective way to measure concentrations of the substances from which the templates are derived.)

Various other features can be incorporated into the tool, including outfitting the tool with a reservoir of a reference fluid for downhole calibration of the system and for compensating for contamination on the windows of the flow cell. A shock and vibration monitoring system (e.g., an accelerometer that is mounted to the tool and periodically sensed by the processing electronics) can be used to detect periods of high vibration that might make measurements less reliable. Measurements collected during these periods can be discarded or given a lower weighting that reflects their reduced reliability. Scattered light can be analyzed to determine the size distribution of particles entrained in a fluid flow. An ultraviolet light source can be included to induce fluorescence in the material, which fluorescence can be analyzed to aid in determining composition of the sample. To monitor the spectrum and intensity of the light source, a bypass path can be provided to direct light to a detector without passing through the sample cell. In some embodiments, a collection of varied detector types can be used, with filters, dichroic mirrors or other distribution means used to split the received light into bands best suited to be measured by the individual detectors.

Numerous variations and modifications will become apparent to those skilled in the art once the above disclosure is fully appreciated. It is intended that the following claims be interpreted to embrace all such variations and modifications.

What is claimed is:

1. A downhole tool that comprises:
a downhole light detector;
a downhole dual-beam interferometer on an optical path between two light sources and the light detector, wherein the interferometer produces, from light received along the optical path, a spectralized beam having a spectral composition with multiple frequency components measurable from time variations of the spectralized beam's intensity;
a window on the optical path that enables light received along the optical path to illuminate a material to be analyzed, wherein the material is a borehole fluid or part of a borehole wall; and
processing electronics coupled to the light detector to detect an electrical signal representing time variations of the spectralized beam's intensity and to determine therefrom the multiple frequency components and a parameter of the material.

2. The tool of claim 1, wherein the material is a fluid drawn from a port seated against a borehole wall.

3. The tool of claim 2, wherein the window is on a sample cell that stores the fluid for transport to the surface, and the optical path passes through the fluid.

4. The tool of claim 2, wherein the parameter is a contamination level for the fluid.

5. The tool of claim 2, wherein the parameter includes a quantity of at least one fluid type.

6. The tool of claim 2, wherein the parameter includes a concentration of at least one substance.

7. The tool of claim 2, wherein the parameter is a size distribution of particles in the fluid.

8. The tool of claim 1, wherein the parameter is a fluid density or a quantity of at least one fluid type.

9. The tool of claim 1, wherein the light detector senses light reflected from the material.

10. The tool of claim 1, wherein the light detector senses light transmitted through the material.

11. The tool of claim 1, wherein the interferometer includes an integrated light path component comprised of a solid block of a transparent material.

12. The tool of claim 1, wherein one of the two light sources is a reference light source providing light that traverses at least that portion of the light path that includes the interferometer and the light detector, wherein the processing electronics determine a motion compensation based on measurements of light from the reference light source.

13. The tool of claim 1, wherein the tool is adapted to be part of at least one of: a wireline logging assembly, a drilling assembly, and a tubing-conveyed logging assembly.

14. The tool of claim 1, wherein the processing electronics correlate the signal with one or more templates to determine a relative concentration of at least one substance.

15. The downhole tool of claim 1, wherein the interferometer comprises a fixed mirror and a movable mirror, wherein the movable mirror is movable as a function of time to spectralize the light received along the optical path to produce the spectralized beam as a function of time.

16. The downhole tool of claim 1, wherein the interferometer produces the spectralized beam using a reciprocating or rotating mirror, and wherein the processing electronics determine the multiple frequency components using mirror position as a function of time.

17. A downhole tool that comprises:
a downhole light detector;
a downhole interferometer on an optical path between a broadband light source and the light detector, wherein the interferometer produces, from light received along the optical path, a spectralized beam having a spectral composition with multiple frequency components measurable from time variations of the spectralized beam's intensity;
a window on the optical path that enables light received along the optical path to illuminate a material to be analyzed, wherein the material is a borehole fluid or part of a borehole wall; and
processing electronics coupled to the light detector to detect an electrical signal representing time variations of the spectralized beam's intensity and to determine therefrom the multiple frequency components and a parameter of the material,
wherein the interferometer includes a spinning retroreflector having a position encoder coupled to the processing electronics.

18. A downhole analysis method that comprises:
directing light from two downhole light sources along an optical path that includes a downhole interferometer and a window for downhole sample illumination, wherein the downhole sample is a borehole fluid or part of a borehole wall;
modulating one arm length of the interferometer as a function of time to produce a spectralized beam before the light reaches a downhole detector, the spectralized beam having a spectral composition with multiple frequency components measurable from time variations of the spectralized beam's intensity;
measuring time variations of the spectralized beam's intensity with the downhole detector; and
using the measured time variations of the spectralized beam's intensity to determine the multiple frequency components and a property of the downhole sample.

19. The method of claim 18, wherein the downhole sample is a fluid drawn from a port seated against a borehole wall.

20. The method of claim 18, wherein the property is at least one of: a contamination level, a quantity of at least one fluid type, a concentration of at least one substance, and a size distribution of particles.

21. The method of claim 18, wherein modulating one arm length of the interferometer as a function of time comprises reciprocating or rotating a mirror, and wherein mirror position as a function of time is used to determine the multiple frequency components.

22. The method of claim 18, wherein one of the two light sources is a reference light source providing light that traverses at least the interferometer and a light detector, wherein using the measured time variations of the spectralized beam's intensity to determine the multiple frequency components and a property of the downhole sample is based on measurements of light from the reference light source.

* * * * *